United States Patent [19]

Wilhelm et al.

[11] Patent Number: 5,382,667

[45] Date of Patent: Jan. 17, 1995

[54] SUBSTITUTED SUCCINIMIDES AS CORROSION INHIBITORS

[75] Inventors: Didier Wilhelm, Issy Les Moulineaux; Michel Soreau, Barbizon; Alain Blanc, Saint Denis, all of France

[73] Assignee: Societe Francaise Hoechst, Puteaux, France

[21] Appl. No.: 178,532

[22] Filed: Jan. 5, 1994

[30] Foreign Application Priority Data

Jan. 11, 1993 [FR] France ................... 93 00161

[51] Int. Cl.$^6$ ................... C07D 413/06; C23F 11/00
[52] U.S. Cl. ................... 544/141; 252/392; 548/546
[58] Field of Search .......... 544/141; 548/546; 252/392

[56] References Cited

U.S. PATENT DOCUMENTS 3,762,873  10/1973  Alink .

FOREIGN PATENT DOCUMENTS 0026878  4/1981  European Pat. Off. .
0191952  8/1986  European Pat. Off. .
1373411  11/1974  United Kingdom .

OTHER PUBLICATIONS

Malfer, Chemical Abstracts, vol. 114, No. 231911 (1991).

Primary Examiner—Robert W. Ramsuer
Attorney, Agent, or Firm—Browdy and Neimark

[57] ABSTRACT

Substituted succinimides of formula (I)

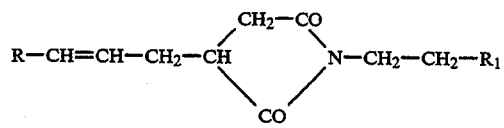

in which R represents an alkyl radical containing 5 to 15 carbon atoms and $R_1$ represents an oxo-2 morpholino radical or a (carboxymethyl)(hydroxy-2 ethyl) amino radical and their salts, and use for obtaining concentrates intended for metal-working, particularly for combatting corrosion.

12 Claims, No Drawings

SUBSTITUTED SUCCINIMIDES AS CORROSION INHIBITORS

The present invention relates to substituted succinimides, a process for their preparation and their use as corrosion inhibitors.

In the field of metal-working, corrosion inhibitors are commonly used in solution or in suspension in generally aqueous systems. As corrosion inhibitors, it is known to use salts of alkaline metals or alkanol amine of various mineral or organic acids such as sodium nitrite, dipotassium phosphate, barium metaborate, sodium benzoate, free or salified amic acids such as substituted succinamic or maleamic acids (cf. Kirk-Othmer, Encyclopedia of Chemical Technology, Vol. 7, page 137, 3rd edition, John Wiley and Sons, New York, 1984, U.S. Pat. Nos. 3 394 145, 3 646 151, 4 053 426, 4 130 433, 4 148 605, 4 235 874, 4 326 987, 4 332 737, 4 737 159, European Patent Application Nos. 106 234, 127 132, 191 952, 216 280, 359 048, 464 473, 501 318). All these products, although active, do however have a certain number of disadvantages. Today, corrosion inhibitors are in fact sought which are active, non-toxic, readily recyclable, easily degradable, economic, hydro-soluble or dispersible in water, stable vis-á-vis salts of tap water hardness, respect the environment and do not present any risk to the user.

The known corrosion inhibitors do not entirely satisfy the wishes of users, particularly in terms of cost.

In order to meet these requirements, the applicant has surprisingly discovered novel substituted succinimides having useful anti-corrosive properties.

The present invention has as its subject products of formula (I):

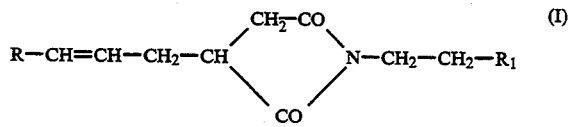

in which R represents an alkyl radical containing 5 to 15 carbon atoms and $R_1$ represents an oxo-2-morpholino radical or a (carboxymethyl)(hydroxy-2 ethyl) amino radical, in their cis and/or trans, racemic or optically active forms, as well as the salts of alkaline or alkaline earth metals or amines of the products of formula (I) in which R has the meaning already given and $R_1$ represents a (carboxymethyl)(hydroxy-2 ethyl) amino radical.

The expression alkyl containing 5 to 15 carbon atoms may describe for example a pentyl, hexyl, heptyl, octyl, nonyl, decyl, undecyl, dodecyl, tridecyl, tetradecyl, pentadecyl radical.

The amine salts of the products of formula (I) in which R has the meaning already given and $R_1$ represents a (carboxymethyl) (hydroxy-2 ethyl) amino radical are the salts of ordinary amines. Among ordinary amines can, for example, be cited alkanol amines such as triethanolamine, monoethanolamine. The salts of alkaline metal salts of the products of formula (I) in which R has the meaning already given and $R_1$ represents a (carboxymethyl) (hydroxy-2 ethyl) amino radical are preferably those of sodium or potassium.

More particularly, the invention has as its subject the products as defined above, characterized in that in formula (I) R represents a n-pentyl, n-nonyl or n-pentadecyl radical and $R_1$ has the meaning already given previously, in their cis and/or trans, racemic or optically active forms, as well as the salts of alkaline or alkaline earth metals or amines of products of formula (I) in which R has the meaning already given and $R_1$ represents a methyl (carboxy methyl)(hydroxy-2 ethyl) amino radical.

Among these latter products, the following can be cited more particularly:

(octene-2-yl)-3 N-[(oxo-2-morpholino)-2-ethyl] succinimide, (dodecene-2 yl)-3 N-[(oxo-2-morpholino)-2-ethyl] succinimide, (octodecene-2-yl)-3 N-[(oxo-2 morpholino)-2-ethyl] succinimide, and N-(hydroxy-2-ethyl) N-[((octene-2 yl)-3 succinimido)-2 ethyl] glycine, N-(hydroxy-2 ethyl) N-[((dodecene-2 yl)-3 succinimido)-2 ethyl] glycine, N-(hydroxy-2 ethyl) N-[((octodecene-2 yl)-3 succinimido)-2 ethyl] glycine as well as their salts of alkaline or alkaline earth metals, monoethanolamine and/or triethanolamine.

According to the invention, the products of formula (I) above and their salts can be prepared by a process characterized in that glyoxal is reacted on the product of formula (II):

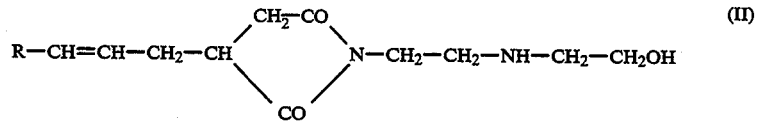

in which R has the meaning already given previously in order to obtain a product of formula $I_A$ corresponding to a product of formula I in which R has the meaning already given and $R_1$ represents an (oxo-2 morpholino) radical:

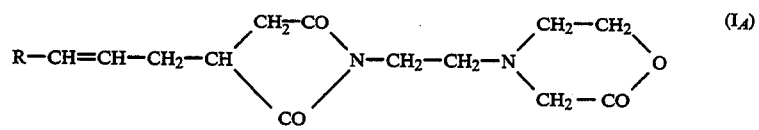

which is either isolated, or, if desired, hydrolyzed for example by simple heating in aqueous medium, in order to obtain a product of formula ($I_B$) corresponding to a product of formula (I) in which R has the meaning already given and $R_1$ represents a ((carboxymethyl)(hydroxy-2 ethyl) amino) radical.

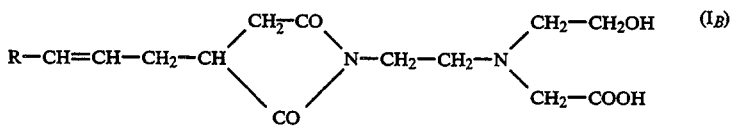

which is isolated and, if desired, salified according to the usual methods.

The products of formula (II) are known products or ones which can be easily obtained by the condensation of N-(hydroxy-2 ethyl) ethylene diamine on corresponding substituted succinic anhydride of formula (III) in which R has the meaning already given (cf. European Patent Application No. 417,990).

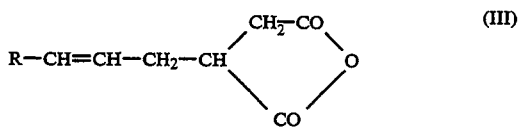

The majority of the products of formula (III) are commercially available products and they can be prepared easily by reacting maleic anhydride with the alkene of formula (IV):

$$R-CH_2-CH=CH_2 \qquad (IV)$$

in which R has the meaning already given.

In the preferred conditions for implementation, the process described above is carried out in the following manner:
- the condensation of the glyoxal with the product of formula (II) is carried out at a temperature between 50° and 80° C., using up to 25% excess of glyoxal in a 40% by weight aqueous solution.
- the hydrolysis of the product of formula ($I_A$) is carried out by simple heating in 3 to 5 parts by weight of water at a temperature between 40° and 100° C.

The invention equally has as its subject concentrates containing one or more products of formula (I) above in solution either in water or in water possibly containing a monoalkyl ether of a glycol such as monobutyl ether diethylene glycol, hereinafter called BDG, or in an emulsion of water in oil.

These concentrates contain, as well as one or more products of formula (I) above at a concentration by weight above or equal to 20%, one or more basic agents selected from the group consisting of sodium hydroxide, potassium hydroxide, monoethanolamine, hereinafter called MEA, triethanolamine, hereinafter called TEA. Examples of these concentrates are given in Table I in which the nature of the product of formula (I) used, referred to by its number given in the examples, is given in line A, its weight expressed as the product as such is given in line B and its weight expressed as dry product is given in line C; the weights expressed in dryness of the product of formula (I) and the different basic agents used are given at line MA. Oil 01 is a commercially available oil, the carbons distribution of which, according to ASTM standard D 2140, is Ca=12.3%, Cp=47.3% and Cn=40.4%, density 0.9 and refractive index 1.4936 at 20° C. The expressions KOH at 50% and NaOH at 50% mean potassium hydroxide or sodium hydroxide at 50% by weight in water. The pH values of an aqueous solution containing 5% by weight of MA in tap water are given in line pH.

All the quantities given in Table I are expressed in grammes.

The quantity of basic agent(s) introduced into the concentrate according to the present invention is determined in such a way that after its dilution with tap water to a concentration of 5% by weight MA, the pH of the aqueous solution obtained is between 7 and 10, preferably between 9 and 10.

The products of formula (I) above in their cis, trans, racemic and/or optically active forms as well as the salts of alkaline, alkaline earth metal or amines of the products of formula (I) in which R has the meaning already given and $R_1$ represents a (hydroxy-2 ethyl)-(carboxymethyl) amino radical have useful anti-corrosive properties.

These properties justify the use of the substituted succinimides above as well as their salts for obtaining concentrates intended for metal-working and the inhibition of the corrosion of metals.

In particular, these properties are brought to light by the test described in DIN standard 51360, page II, using grey cast iron turnings with reference GG25. The results of this test carried out starting from different concentrates according to the present invention, after their dilution with tap water to a concentration by weight of MA of 1 to 5% are given in Table II, in which grades from 0 to 5 are given, according to the concentration of MA of the concentrates C1–C10; 0 indicates zero corrosion and 5 substantial corrosion.

On examining this table, it is noted that the concentrates C4–C6 at a concentration of 2% of MA in tap water protect the cast iron very effectively against corrosion. In this test, the product of formula (I) which is most active is N-(hydroxy-2-ethyl) N-[((octene-2 yl)-3 succinimido)-2 ethyl] glycine.

The $^{13}C$ NMR spectra of the products described in the examples were recorded with a BRUCKER AC100 apparatus at 25 MHz or 50 MHz.

The chemical shifts shown involve only certain carbon atoms to the exclusion of carbon atoms in the chain R—CH=CH—CH$_2$—and the methine and methylene carbon atoms of the succinimide ring.

The following examples illustrate the present invention without however limiting it.

EXAMPLE 1

(octene-2 yl)-3 N[(oxo-2 morpholino)-2 ethyl] succinimide.

Stage 1

1 mole (104.15 g) of N-(hydroxy-2 ethyl) ethylenediamine is introduced slowly with vigorous agitation and maintaining the temperature of the reaction medium at 70° C., into 1 mole (210.26 g) of (octene-2 yl)-1 succinic anhydride. Once the introduction has been completed stirring continues for one hour at 70° C., then for 50 minutes at 150° C., all the while distilling the water formed under reduced pressure.

After cooling of the reaction medium to 20° C., 296 g of (octene-2 yl)-3 N[(hydroxy-2 ethyl) amino-2 ethyl]

succinimide 11 (II with R=n-pentyl) is obtained in the form of an oil.

Analyses $C_{16}H_{28}N_2O_3$ 296.39 N % 9.3 (theory 9.45) Water determination (K. Fisher): 0.3% $^{13}C$ NMR (DMSO, d$_6$, ppm): 179.5; 176.6; 60.3; 51.2; 46.5; 37.9.

Stage 2

98 g of a 40% by weight aqueous glyoxal solution, that is 0.676 moles, are introduced over 30 minutes with agitation whilst maintaining the temperature of the reaction medium at 80° C. into 200 g (0.675 mole) of 11 prepared in Example 1, stage 1. Once the introduction has been completed, stirring continues for 2 hours at 80° C., then the water formed is eliminated by distillation under reduced pressure. After cooling of the reaction medium to 20° C. 225 g (0.67 moles) of (octene-2 yl)-3 N[(oxo-2 morpholino)-2 ethyl] succinimide, 12 (($I_A$) with R=n-pentyl) are obtained in the form of a very thick oil.

Analyses $C_{16}H_{28}N_2O_4$ 336.41 N% 8.2 (theory 8.33) Water determination (K. Fisher): 0.7 % $^{13}C$ NMR(DMSO, d$_6$, ppm): 179.4; 176.5; 166.9; 68.5; 55.1; 53.1; 47.0; 34.9. This oil distils at 220°–230° C. under a pressure of 50 Pa.

EXAMPLE 2

N-(hydroxy-2 ethyl) n-[(octene-2 yl)-3 succinimido)-2 ethyl] glycine 50.5 g (149 mmoles) of 12 prepared in Example 1, stage 2 are heated for 3 hours with agitation at 40° C. then for one hour at 65° C. and finally for 1 hour at boiling, in 150 g of distilled water. After cooling of the reaction medium to ambient temperature, 200 g of an aqueous solution containing 52.8 g (149 mmoles) of N-(hydroxy-2 ethyl) N-[(octene-2 yl)-3 succinimido)-2 ethyl] glycine, 13, (($I_B$) with R=n-pentyl)) are obtained.

This aqueous solution contains 73.7% water determined by quantitative analysis according to K. Fisher, 2.1% of nitrogen and a given acidimetric determination content of 0.64 meq/g (theory 0.74 meq/g).

Analysis $^{13}C$ NMR (DMSO, d$_6$, ppm): 181; 178.2; 171.3; 58.1; 56.6; 56.3; 52.1; 35.6.

EXAMPLE 3

(dodecene-2 yl)-3 N[oxo-2 morpholino-2 ethyl] succinimide.

Stage 1

Stage I of example 1 is repeated starting with 1 mole of (dodecene-2 yl)-1 succinic anhydride and 1 mole of N-(hydroxy-2 ethyl) ethylenediamine. In this way 352 g of (dodecene-2 yl)-3 N[(hydroxy-2 ethyl) amino-2 ethyl] succinimide, 21, ((II) with R=n-nonyl) are obtained in the form of an oil.

Analyses $C_{20}H_{36}N_2O_3$ 352.51 N% 7.6 (theory 7.95) Water determination (K. Fisher): 0.55% $^{13}C$ NMR(DMSO, d$_6$, ppm): 180; 178 solid; 176.5; 60.2; 51.1; 46.1; 37.9. This oil is used as it is for stage 2.

Stage 2

Stage 2 of example 1 is repeated starting from 0.675 mole (239 g) of 21 prepared in stage 1 above and 0.675 moles of glyoxal in a 40% by weight aqueous solution. In this way 278 g of (dodecene-2 yl)-3 N[oxo-2 morpholino)-2 ethyl] succinimide, 22 (($I_A$) with R=n-nonyl)) are obtained in the form of an oil.

Analyses $C_{22}H_{36}N_2O_4$ 392.52 N% 6.8 (theory 7.14) Water determination (K. Fisher): 4.9% $^{13}C$ NMR (DMSO, d6, ppm): 180–178 solid; 176.3; 166.7; 68.5; 55.1; 53.2; 48; 34.7.

EXAMPLE 4

N-(hydroxy, 2 ethyl) N-[((dodecene-2 yl)-3 succinimido)-2 ethyl glycine.

Example 2 is repeated starting from 128 mmoles of 22 prepared in Example 2, stage 2 and 149 g of water. 201.7 g of a coloured aqueous solution containing 128 mmoles (52.5 g) of N-(hydroxy-2 ethyl) N-[((dodecene-2 yl)-3 succinimido)-2 ethyl] glycine, 23, (($I_B$) with R=n-nonyl) are obtained in this way. This aqueous solution contains 74% water determined by analysis according to K. Fisher, 1.9% nitrogen and the acidimetric determination content is 0.64 meq/g (theory 0.64 meq/g).

Analysis $^{13}C$ NMR (acetone, d$_6$, ppm): 182–178 solid; 178; 170; 57.2; 56.7; 56.5; 53.1; 34.4.

EXAMPLE 5

(octadecene-2 yl)-3 N-[(oxo-2 morpholino)-2 ethyl] succinimide.

Stage 1

Stage 1 from Example 1 is repeated starting with 1 mole of (octadecene-2 yl)-i succinic anhydride and 1 mole of N-(hydroxy-2 ethyl) ethylenediamine. In this way 436 g of (octadecene-2 yl)-3 N-[(hydroxy-2 ethyl) amino-2 ethyl] succinimide, 31, ((II) with R=n-pentadecyl) are obtained in the form of an oil.

Analyses $C_{26}H_{48}N_2O_3$ 436.66 N% 6.8 (theory 6.42) Water determination (K. Fisher): 1.4% $^{13}C$ NMR (DMSO, d$_6$, ppm): 177; 174.5; 60; 51; 47.5 (one signal is merged with that of the DMSO).

Stage 2

Stage 2 of Example 1 is repeated starting with 0.675 moles (299 g) of 31 prepared in stage 1 above and 0.675 moles of a 40% by weight aqueous solution of glyoxal. 325.6 g of (octadecene-2 yl)-3 N-[(oxo-2 morpholino)-2 ethyl] succinimide, 32 (($I_A$) with R=n-pentadecyl) are obtained in the form of an oil.

Analyses $C_{28}H_{48}N_2O_4$ 476.68 N% 6.3 (theory 5.88) Water proportion (K. Fisher): 1.2% $^{13}C$ NMR (DMSO, d$_6$, ppm): 179.3; 176.4; 166.9; 68.5; 55.1; 53.2; 47.9; 35.

EXAMPLE 6

Example 2 is repeated starting with 34 mmoles (16.4 g) of 32 prepared in Example 3, stage 2 and 45 g of distilled water. Approximately 61 g of a coloured paste containing 34 mmoles (16.8 g) of N-(hydroxy-2 ethyl) N-[(octadecene-2 yl)-3 succinimido)-2 ethyl] glycine, 33, (($I_B$) with R=n-pentadecyl) are obtained in this way.

TABLE I

| | Compositions by weight of the concentrates | | | | | | | | | |
|---|---|---|---|---|---|---|---|---|---|---|
| | C1 | C2 | C3 | C4 | C5 | C6 | C7 | C8 | C9 | C10 |
| A | 12 | 22 | 32 | 13 | 13 | 13 | 13 | 23 | 23 | 33 |
| B | 69 | 62,5 | 41,5 | 88 | 92,2 | 88,4 | 96 | 88,5 | 91,9 | 88,3 |
| C | 68,5 | 59,4 | 41 | 23,14 | 24,24 | 23,25 | 25,24 | 23,0 | 23,9 | 24,28 |
| MEA | 10,3 | 6,25 | 4,5 | 5,1 | | | | 4,3 | | 2,9 |
| TEA | 20,7 | 18,75 | 12,5 | 6,9 | | 7,0 | | 7,2 | | 8,8 |

TABLE I-continued

| | Compositions by weight of the concentrates | | | | | | | | | |
|---|---|---|---|---|---|---|---|---|---|---|
| | C1 | C2 | C3 | C4 | C5 | C6 | C7 | C8 | C9 | C10 |
| KOH at 50% | | | | | 7,8 | | 4 | | 3,1 | |
| NaOH at 50% | | | | | | 4,6 | | | | |
| M.A | 99,5 | 84,4 | 58 | 35,14 | 28,14 | 32,55 | 27,24 | 34,5 | 25,45 | 35,98 |
| Tap water | | 12,5 | | | | | | | | |
| Oil Ol | | | 41,5 | | | | | | | |
| BDG | | | | | | | | | 5 | |
| Total weight | 100 | 100 | 100 | 100 | 100 | 100 | 100 | 100 | 100 | 100 |
| pH | 9,2 | 9,1 | 9,0 | 9,2 | 9,1 | 9,0 | 7,1 | 9,3 | 7,25 | 9,3 |

TABLE II

Results of the corrosion tests as a function of the dilution of various concentrates.

| | Concentrates | | | | | | | | | |
|---|---|---|---|---|---|---|---|---|---|---|
| Concentrations | C1 | C2 | C3 | C4 | C5 | C6 | C7 | C8 | C9 | C10 |
| 1% | | | | | 4 | 4 | | | | |
| 1,5% | | | 4 | 1 | 4 | 4 | | | | |
| 2% | | 3 | 0 | 0 | 0 | | 2 | 4 | | |
| 2,5% | | | | | 0 | 0 | | | | |
| 3% | | | | | | | | 4 | | |
| 3,5% | | | | | | | | | | |
| 4% | | 1 | | | | 1 | | 4 | | 1 |
| 4,5% | | | | | | | | | | |
| 5% | 2 | 0 | 0 | 0 | | | 0 | 0 | 4 | 1 |

We claim:
1. Substituted succinimides of formula (I)

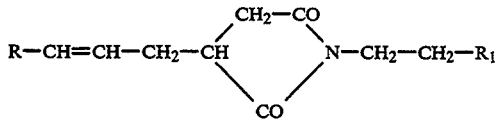

in which R represents an alkyl radical containing 5 to 15 carbon atoms and $R_1$ represents an oxo-2 morpholino radical or a (carboxymethyl) (hydroxy-2 ethyl) amino radical.

2. Salts of alkaline, alkaline-earth metals or amine of succinimides as defined in claim 1 characterized in that in formula (I), R represents an alkyl radical containing 5 to 15 carbon atoms and $R_1$ represents a (carboxymethyl)(hydroxy-2 ethyl) amino radical.

3. (Octene-2 yl)-3 N-[(oxo-2 morpholino)-2 ethyl] succinimide.

4. (Dodecene-2 yl)-3 N-[(oxo-2 morpholino)-2 ethyl] succinimide.

5. (Octodecene-2 yl)-3 N-[(oxo-2 morpholino)-2 ethyl] succinimide.

6. N-(hydroxy-2 ethyl) N-[((dodecene-2 yl)-3 succinimido)-2 ethyl] glycine or its salts of alkaline, alkaline earth metals, monoethanolamine or triethanolamine.

7. N-(hydroxy-2 ethyl) N-[((octene-2 yl)-3 succinimido)-2 ethyl] glycine or its salts of alkaline, alkaline earth metals, monoethanolamine or triethanolamine.

8. N-(hydroxy-2 ethyl) N-[((octadecene-2 yl)-3 succinimido)-2 ethyl glycine or its salts of alkaline, alkaline earth metals, monoethanolamine or triethanolamine.

9. Salts according to claim 2 characterized in that they are salts of amines selected from the group comprising monoethanolamine and triethanolamine.

10. A salt according to claim 2 of an alkali metal selected from the group consisting of sodium and potassium.

11. An aqueous concentrate comprising a compound according to claim 1.

12. An aqueous concentrate according to claim 11, comprising at least 20% by weight of said compound.

* * * * *